United States Patent [19]

Smith

[11] 4,065,556

[45] Dec. 27, 1977

[54] TUBERCIDIN PREPARATION

[75] Inventor: Charles G. Smith, Kalamazoo, Mich.

[73] Assignee: The Upjohn Company, Kalamazoo, Mich.

[21] Appl. No.: 689,474

[22] Filed: May 24, 1976

Related U.S. Application Data

[63] Continuation of Ser. No. 557,759, March 12, 1975, abandoned, which is a continuation of Ser. No. 435,272, Jan. 21, 1974, abandoned, which is a continuation of Ser. No. 278,836, Aug. 8, 1972, abandoned, which is a continuation of Ser. No. 113,656, Feb. 8, 1971, abandoned, which is a continuation of Ser. No. 810,925, March 24, 1969, abandoned, which is a continuation of Ser. No. 529,664, Aug. 9, 1967, abandoned.

[51] Int. Cl.$^2$ .................... A61K 31/71; A61K 31/70; A61K 35/14

[52] U.S. Cl. .................................. 424/181; 424/180; 424/101

[58] Field of Search ................ 424/101, 116, 180, 181

[56] References Cited

PUBLICATIONS

Grage et al., Cancer Research, 30, pp. 79–81, Jan. 1970.
The Merck Index, 9th Ed., Merck & Co., Inc., Rahway, N.J., 1976, p. 1257.

Primary Examiner—Jerome D. Goldberg
Attorney, Agent, or Firm—John J. Killinger; Roman Saliwanchik

[57] ABSTRACT

A process for preparing tubercidin in a more acceptable form for injection consisting of mixing whole blood with a saline solution of tubercidin.

2 Claims, No

TUBERCIDIN PREPARATION

CROSS REFERENCE TO RELATED APPLICATIONS

This application is a continuation of application Ser. No. 557,759, filed Mar. 12, 1975, now abandoned which in turn is a continuation of application Ser. No. 435,272, filed Jan. 21, 1974, now abandoned, which in turn in a continuation of application Ser. No. 278,836, filed Aug. 8, 1972, now abandoned, which in turn is a continuation of application Ser. No. 113,656, filed Feb. 8, 1971, now abondoned, which in turn is a continuation of application Ser. No. 810,925, filed Mar. 24, 1969, now abandoned, which in turn is a continuation of application Ser. No. 529,664, filed Aug. 9, 1967, now abandoned.

This invention relates to a therapeutic composition, a method for its preparation, and a method for its use. More particularly, this invention relates to therapeutic compositions and methods involving tubercidin-containing blood cells.

Tubercidin is a known antibiotic which can be produced by the methods disclosed in U.S. Pat. No. 3,167,540, issued on Jan. 26, 1965, for the preparation of sparsomycin A, which is another name for tubercidin. Some of its pharmacologic properties are disclosed in J. Antibiotics [A] X:201-204, 1957, and Cancer Chemotherapy Reports, No. 36, March, 1964, 19-22. Thus, tubercidin has been used in the treatment of cancer and Mycosis fungoides and is of considerable interest in other areas of therapy where its cytotoxicity and its unique property of being absorbed selectively by blood cells can come into play. Whatever its ultimate applications in therapy may be, tubercidin is of sufficient interest to make it desirable to prepare tubercidin in a form which will avoid the present difficulties presented by the clinical administration of tubercidin. For example, severe toxicity has occurred at the site of injection in man and animals when tubercidin is administered parenterally. Its "leaking" from the injection site may lead to destruction of the surrounding tissue cells. Tubercidin has also been implicated in kidney toxicity.

The present invention provides a novel therapeutic composition containing blood cells and tubercidin, a method for the preparation of such a composition, and a method of treating mammals and birds with such a composition. Besides reducing toxicity, the invention also provides a means of prolonging the activity of tubercidin.

The therapeutic composition comprises blood cells having tubercidin absorbed therein and an isotonic, intravenously infusable aqueous vehicle therefor. The method of treatment comprises the intravenous administration of such a composition to a warm-blooded subject. The method of preparing the composition comprises contacting a blood cell-containing preparation with tubercidin in vitro, separating blood cells from the vehicle, and combining the blood cells with an isotonic, intravenously infusable aqueous vehicle. This invention, therefore, provides a less toxic means of using tubercidin both to explore its pharmacologic properties and to apply it to therapeutic situations. The method of treatment can be applied to humans and animals.

Many experiments have verified that tubercidin is almost completely absorbed by blood cells, especially the erythrocytes, immediately upon contacting tubercidin with blood in vitro. Both biological assays and radio-active tests have verified this fact. In carrying out the method of preparation, a solution of tubercidin can be added directly to whole blood or to blood cell-containing prepartions, the vehicle for which is compatible both with blood cells and tubercidin. The uptake of tubercidin into the blood cells in relatively rapid and can be accomplished for example in about 30–60 minutes, although time merely affects the proportion of added tubercidin taken up in the blood. A temperature between about room temperature and 37° C. is suitable. Once the tubercidin has been added and incubated for a suitable period of time, the preparation can be centrifuged to separate out the blood cells. The cells are then re-suspended to physiologic saline or other isotonic aqueous vehicle for intravenous use and are ready for infusion. Of course, the finished preparation must be sterile before it can be used.

Preferably, the blood used in making the composition of this invention is withdrawn from the patient to whom the tubercidin is to be administered. The blood is withdrawn by standard hospital laboratory techniques into an appropriate anti-coagulant, and tubercidin dissolved in a sterile aqueous vehicle is added to give a concentration between 50 and 200 mcg./ml. of whole blood. After incubation for 60 minutes at 37° C., the preparation is centrifuged, and the cells are washed with an equal volume of physiologic saline. The cells are then re-suspended in physiologic saline and are ready for infusion into a patient intravenously. The whole process is preferably carried out under aseptic conditions.

When it is desired to use tubercidin at a concentration of 50 or 100 mcg./ml., it is not necessary to wash the cells, since 95 and 90%, respectively, of the added drug is absorbed under these conditions into the cells. At drug concentrations greater than 100 mcg./ml., washing is necessary to remove free tubercidin.

The dosage of tubercidin to be administered by the method of this invention will of course vary with the disease and tolerance of the subject. Thus, in one case, a maximum of 50 mcg./kg. of patient body weight per day may be administered in the form of tubercidin and blood cells, whereas in other cases as much as 1000 mcg./kg. per day or greater may be given with appropriate time intervals between the doses. Such parameters must be determined on an individual basis, depending upon the disease, nutritional state of the patient, and previous toxicity observed in each individual.

Since the life span of a red blood cell is approximately four months in man, relatively large intermittent doses of tubercidin can be administered by this method and be available for slow release to the body for prolonged periods of time. In certain diseases states, two treatments per year may suffice, whereas in other cancer cases weekly treatment will be required. A similar result is obtained in other mammals.

The following example illustrates the best mode contemplated for carrying out the invention but is not to be construed as limiting.

EXAMPLE

Aseptic conditions and techniques are used throughout the following process. A sterile solution of tubercidin is prepared according to conventional pharmaceutical techniques so that each cubic centimeter contains the following types and amounts of ingredients:

Tubercidin: 1 mg.
Sodium chloride, fine crystals AR: 9 mg.
Benzyl alcohol NF: 9 mg.
Water for injection q.s. ad Five cubic centimeters of ethylenediaminetetraacetic acid tetrasodium salt (200 mg./cc.) is added to a 500 cc. blood collection bottle. To this 45 cc. of tubercidin in aqueous solution is added. Three hundred cubic centimeters of blood is drawn from a human cancer patient into the blood collection bottle, mixed carefully, incubated for one hour at 37° C., centrifuged to separate out the blood cells, the blood cells are then made back up to the 300 cc. volume by adding physiological saline. Upon reinfusion into the patient, there is less likelihood of local toxicity at the site of injection as well as kidney toxicity. Prolonged action is also obtained.

What is claimed is:

1. Tubercidin-containing human red blood cells prepared by:
    1. mixing whole blood and a physiological saline solution of tubercidin, the amount of tubercidin providing a concentration of 50 to 200 mcg. per milliliter of the blood;
    2. incubating the mixture of blood and tubercidin for from 30 to 60 minutes at from room temperature to 37° C.; and
    3. centrifuging the incubated mixture to recover the tubercidin-containing red blood cells.

2. Tubercidin containing human red blood cells prepared according to claim 1 and additionally processed by washing to remove free tubercidin.

* * * * *